US010486147B1

(12) United States Patent
Marie-Rose et al.

(10) Patent No.: US 10,486,147 B1
(45) Date of Patent: Nov. 26, 2019

(54) HYBRID EXTRUDED MIXED ZEOLITE CATALYSTS FOR SYNTHESIS OF LIGHT OLEFINS

(71) Applicants: Stephane Marie-Rose, Sherbrooke (CA); Ludovic Pinard, Chauvigny (FR); Jennifer Lorena Gil Coba, Sherbrooke (CA)

(72) Inventors: Stephane Marie-Rose, Sherbrooke (CA); Ludovic Pinard, Chauvigny (FR); Jennifer Lorena Gil Coba, Sherbrooke (CA)

(73) Assignee: Enerkem, Inc., Montreal, Quebec (CA)

( * ) Notice: Subject to any disclaimer, the term of this patent is extended or adjusted under 35 U.S.C. 154(b) by 0 days.

(21) Appl. No.: 16/535,744

(22) Filed: Aug. 8, 2019

Related U.S. Application Data

(62) Division of application No. 15/481,896, filed on Apr. 7, 2017, now Pat. No. 10,406,511.

(60) Provisional application No. 62/320,907, filed on Apr. 11, 2016.

(51) Int. Cl.
| | | |
|---|---|---|
| *C07C 1/20* | (2006.01) | |
| *B01J 29/80* | (2006.01) | |
| *B01J 37/00* | (2006.01) | |
| *B01J 35/00* | (2006.01) | |
| B01J 35/10 | (2006.01) | |
| B01J 29/40 | (2006.01) | |
| B01J 29/65 | (2006.01) | |

(52) U.S. Cl.
CPC ........... *B01J 29/80* (2013.01); *B01J 35/0006* (2013.01); *B01J 37/0009* (2013.01); *B01J 37/0018* (2013.01); *C07C 1/20* (2013.01); *B01J 29/40* (2013.01); *B01J 29/65* (2013.01); *B01J 35/1061* (2013.01); *B01J 2229/42* (2013.01); *C07C 2529/40* (2013.01); *C07C 2529/65* (2013.01); *C07C 2529/80* (2013.01); *Y02P 20/52* (2015.11); *Y02P 30/42* (2015.11)

(58) Field of Classification Search
CPC . C07C 1/20; C07C 11/04; C07C 11/06; Y02P 20/52; Y02P 30/42
USPC ........................................ 585/638, 639, 640
See application file for complete search history.

(56) References Cited

U.S. PATENT DOCUMENTS

| | | |
|---|---|---|
| 6,797,851 B2 | 9/2004 | Martens et al. |
| 7,230,151 B2 | 6/2007 | Martens et al. |
| 2004/0133053 A1 | 7/2004 | Martens et al. |
| 2004/0254413 A1* | 12/2004 | Martens ............... C07C 1/20 585/639 |
| 2005/0130832 A1 | 6/2005 | Abrevaya et al. |

FOREIGN PATENT DOCUMENTS

| | | |
|---|---|---|
| WO | WO2004/056944 | 7/2004 |
| WO | WO2013/034678 | 3/2013 |

* cited by examiner

*Primary Examiner* — Elizabeth D Wood
(74) *Attorney, Agent, or Firm* — Raymond J. Lillie

(57) ABSTRACT

A catalyst for converting dimethyl ether into light olefins, including ethylene and propylene. The catalyst comprises a mixture of two zeolites, ZSM-5 and ZSM-35, intimately mixed and kept in close proximity in a porous extruded binder system. The resulting combination of zeolites demonstrates a synergistic effect with respect to the conversion of the dimethyl ether and has improved resistance to deactivation due to carbon and coke formation than the individual zeolites alone when operating in this reaction. The catalyst is used to produce ethylene and propylene from a feed mixture containing methanol, dimethyl ether and water.

21 Claims, No Drawings

HYBRID EXTRUDED MIXED ZEOLITE CATALYSTS FOR SYNTHESIS OF LIGHT OLEFINS

This application is a divisional of application Ser. No. 15/481,896, filed Apr. 7, 2017, now U.S. Pat. No. 10,406,511, which claims priority based on provisional application Ser. No. 62/320,907, filed Apr. 11, 2016, the contents of which are incorporated by reference in their entireties.

BACKGROUND OF THE INVENTION

Field of the Invention

The invention relates to the composition, manufacture, and use of new catalysts that have improved resistance to coke formation and extended catalytic activity for producing light olefins from oxygen-containing organic materials that are obtained from sustainable and fossil resources.

Description of Related Art

Light olefins such as ethylene and propylene are produced as by-products in gasoline production and/or by steam cracking processes, including steam cracking of light alkanes. If a refinery produces significant amounts of aromatic products, however, light olefins, such as ethylene and propylene, to satisfy demand can be produced.

Moreover, in the context of fossil fuel resources and the progressive depletion of oil reserves, alternative and novel routes for production of light olefins from alternative feedstock sources become increasingly important.

Methanol is a building block molecule, also known as a platform chemical that can be used in different applications such the manufacture of formaldehyde according to EP2192102, U.S. Pat. No. 3,987,107, EP0988269, EP1062195; or gasoline manufacture according to WO 2014/063758, U.S. Pat. No. 9,028,567; or Dimethyl ether (DME) production according to U.S. Pat. No. 6,924,399 and US2012/0220804.

Methanol can be used to produce light olefins in a methanol to olefin process. The methanol to gasoline (MTG) technology was developed by Mobil Oil in the 1970's. This technology used mordenite framework inverted, or MFI, type zeolites as catalysts, but it was not until the development of SAPO-34 and similar SAPO (aluminophosphate or zeotyp) catalysts, that methanol to olefin (MTO) conversion became highly selective to light olefins. The mechanism of such processes has been studied widely and a number of postulates have been presented.

Dimethyl ether is a key intermediate for producing light olefins from methanol. The dimethyl ether is formed by a methanol dehydration reaction.

$$2CH_3OH \rightleftharpoons CH_3OCH_3 + H_2O \qquad (1)$$

Reaction 1 shows the dehydration reaction which proceeds as an equilibrium reaction in which maximum conversion of the methanol is about 80%. Unconverted methanol can be separated from the reaction products, such as water, and then recirculated in the dehydration reactor, or used as an oxygenate molecule in the feed for the synthesis of light olefins herein described.

There are a number examples of processes that use methanol as a feedstock for synthesizing light olefins. These are described in US2005/025236, WO2013/034678, WO2004/056944 and US 2003/0078463.

US2005/025236 describes a process for the production of light olefins from methanol and optionally syngas through a dimethyl ether intermediate. The process converts methanol and or syngas into dimethyl ether and water in the presence of acidic γ-alumina, a modified mordenite, zeolite, a ZSM-5 zeolite, sulfonic acid ion exchange resin and a perfluorinated sulfonic acid ionomer catalyst or other catalyst and then in a second step converting the dimethyl ether to light olefin and water in the presence of a second catalyst optionally comprising a molecular sieve or zeotyp and zeolite selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ZSM-5, metal containing forms thereof, intergrown forms thereof, AEI zeolite/chabazite (CHA) zeolite intergrowths, and mixtures thereof.

WO2013/034678 describes a methanol to olefin process in which a feed consisting of methanol and ethanol is reacted over a ZSM-5 zeolite catalyst and is converted to a light olefin product containing ethylene and propylene.

WO2004056944 describes a process for producing propylene and ethylene rich mixtures from olefinic hydrocarbon streams and the relevant catalytic systems used.

U.S. Pat. No. 7,230,151, granted to ExxonMobil Chemical Patents Inc., describes a two catalyst process for making olefins, particularly ethylene and propylene, from an oxygenate feed. The process uses two or more catalysts with the first catalyst containing ZSM-5 and a second catalyst containing ZSM-22, ZSM-23, ZSM-35, ZSM-48, and mixtures thereof.

Al-Dughaither et al. (H. de L. Abdullah S. Al-Dughaither, Neat dimethyl ether conversion to olefins (DTO) over HZSM-5: Effect of $SiO_2/Al_2O_3$ on porosity, surface chemistry, and reactivity, Fuel. 138 (2014) 52-64.) stress the many advantages of using DME instead of methanol for synthesis light olefins. These advantages lead the synthesis to be economical if the DME is produced directly from the syngas (lower equipment cost) and also reduce thermodynamic constraints, lowering the $H_2/CO$ molar ratio to close to 1 for the direct synthesis of DME while methanol synthesis operates usually at a ratio above 2.

Catalysts used for the synthesis of light olefins are zeolite based catalysts. Several zeolites suitable for catalyzing the production of light olefins are ZSM-5, ZSM-35, and MOR. ZSM-35 is also interchangeably referred to as FER as in ferrierite.

Coke formation (a main cause of deactivation) within the catalyst has been identified as a significant drawback, particularly with ZSM-5 zeolite. ZSM-5 for example has a short catalyst operating life of about 600 h before catalytic activity is reduced to an extent that it makes the catalyst unusable. The short life is a result of loss of catalytic activity with time due to coke formation. Carbon as coke is formed on the surface and within the pore structure of the zeolite catalyst and is one of the main causes for the loss of catalytic activity as coke formation results in a progressive loss of catalytic activity and progressive deactivation of the zeolite catalyst with time. Another non-limiting example of coke formation is the deposit of aromatic and/or polyromantic molecules within the pores of the catalyst. For example, the formation of coke within the pores of the SAPO-34 catalyst at about 300° C. to about 380° C. may proceed as follows:

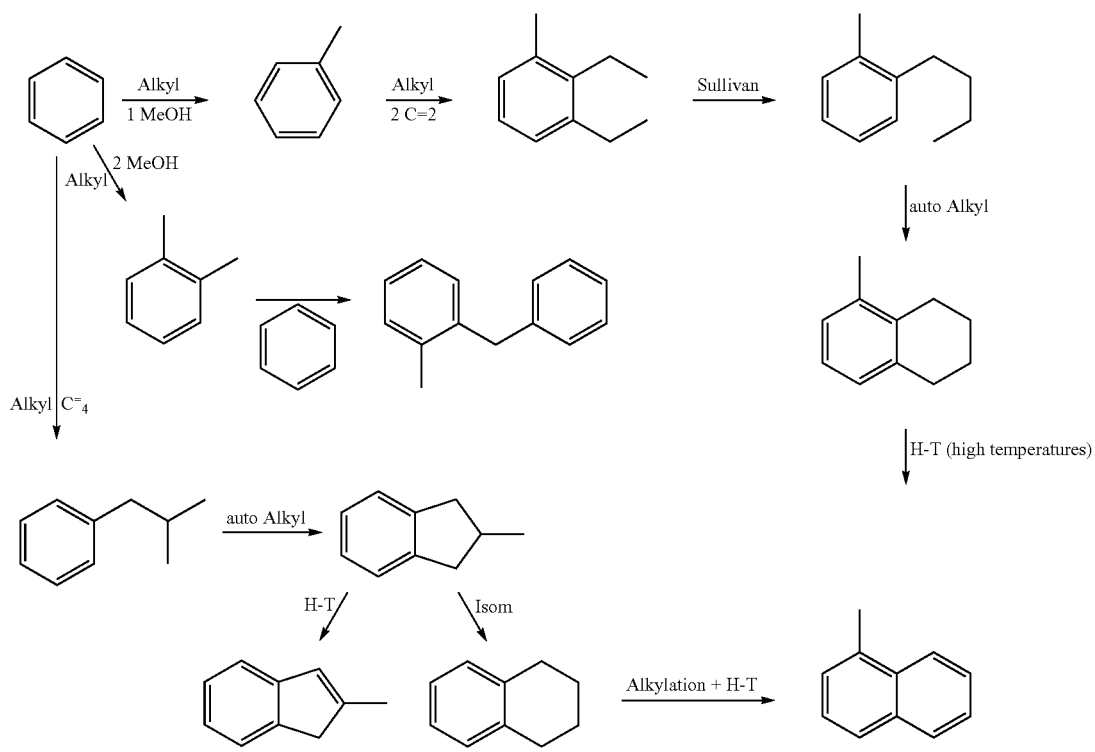

In yet another non-limiting embodiment, the formation of coke within the pores of a catalyst may proceed according to the following mechanism:

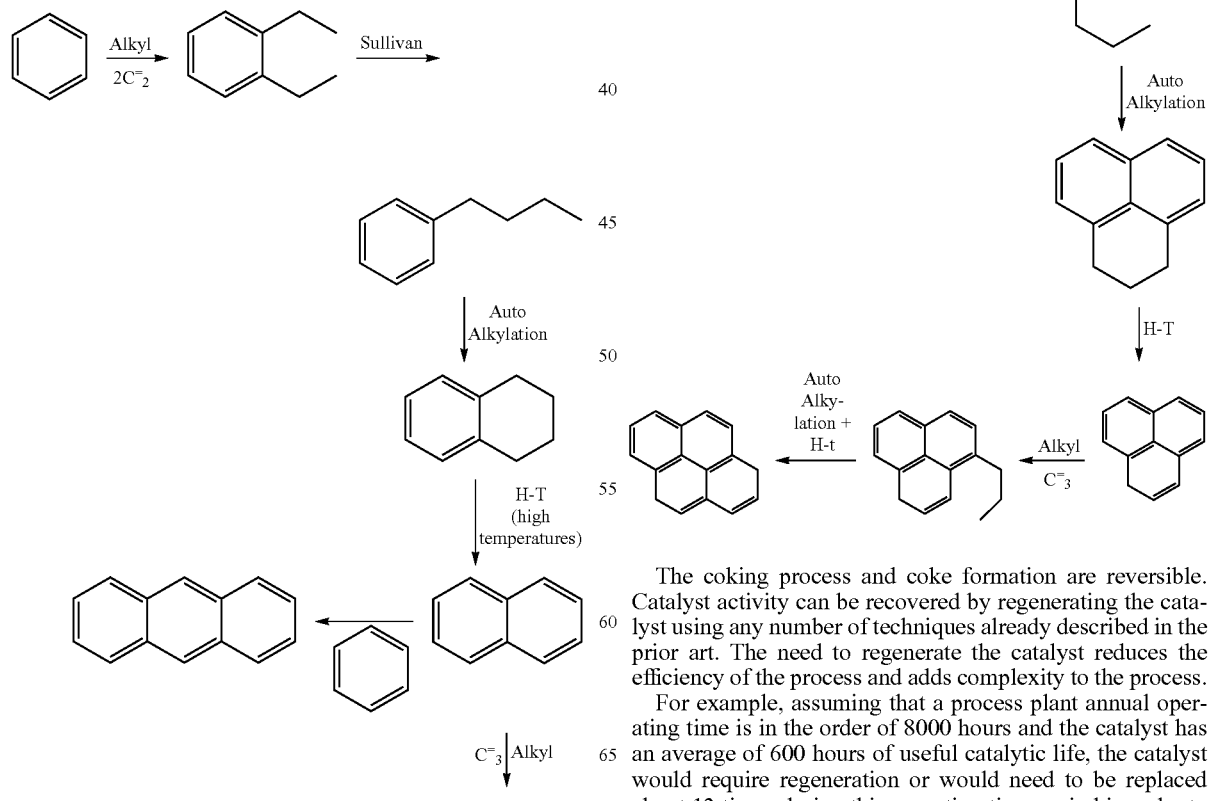

The coking process and coke formation are reversible. Catalyst activity can be recovered by regenerating the catalyst using any number of techniques already described in the prior art. The need to regenerate the catalyst reduces the efficiency of the process and adds complexity to the process.

For example, assuming that a process plant annual operating time is in the order of 8000 hours and the catalyst has an average of 600 hours of useful catalytic life, the catalyst would require regeneration or would need to be replaced about 13 times during this operating time period in order to maintain proper production rates or activity of the catalyst. The rate of catalyst deactivation could be prevented or decreased if it were possible to reduce the rate of formation of the carbon or coke. This in turn would reduce the number of times or frequency by which the catalyst would have to be replaced or regenerated. This leads to an improvement in process efficiency and economic advantages by reducing costs and increasing profitability.

The effects of catalyst deactivation and process requirements for maintaining a steady light olefin production rate can be addressed in several ways. One way of achieving a steady production is to use two or three fixed bed reactors in parallel and cycle their operation with one or two of the reactors producing olefin, and the remaining reactors are placed in standby or regeneration mode.

Alternatively, a fluidized bed reactor with a catalyst regeneration section, similar to a Fluid Catalytic Cracking (FCC) reactor can be used to regenerate a fraction of the catalyst while the remaining fraction is used to produce olefin.

Catalyst regeneration techniques are employed to remove the coke, although it is not necessary to remove all of the coke formed in and on the catalyst because it is known that small amounts of residual coke can enhance catalyst performance. It is believed that complete removal of coke can also lead to degradation of the zeolite (Michel Guisnet and Fernando Ramôa Ribeiro in Deactivation and Regeneration of zeolite catalysts, Catalytic Science Series, Vol 9, 2011, Imperial College Press).

It is also known that water has an effect on the kinetics of coke formation. Water introduced into the reactor with methanol and/or dimethyl ether, DME, reduces coke formation and as a result increases the useful life of the catalyst. Water blocks strong acid sites that are active for oligomerization, H-transfer and cyclization reactions (A G Marchi and G F Froment Catalytic conversion of methanol to light alkenes on SAPO molecular sieves, Applied Catalysis, 71 p.117)

The mechanism referred to as "hydrocarbon pool" and more recently renamed "dual cycle mechanism", attempts to explain the selectively to light olefins synthesis. This is described in the literature (M. Bjorgen, S. Svelle, F. Joensen, J. Nerlov, S. Kolboe, F. Bonino, L. Palumbo, S. Bordiga, and U. Olsbye, *Journal of Catalysis*, 249 (2007) 195-207). The mechanism involves the formation of methylbenzene intermediates at the catalyst active site during ethylene formation. Olefin methylation and cracking is thought to lead to the formation of higher olefins. Aromatic intermediates and higher molecular weight molecules formed in this mechanism also lead to saturated hydrocarbon and coke formation.

The ideal catalysts for methanol to olefin production would be one that produces little coke when used. The ideal catalyst for light olefins synthesis, assuming equal pore structure effect or shape selectivity, would be one that does not form coke and in which the methylbenzene intermediate formation rates are unaffected by high selectively towards the desired light olefins, i.e., propylene or ethylene or mixture of propylene and ethylene.

There is a need for a catalyst that can be used for the production of olefins from methanol and dimethyl ether where the catalyst has a reduced rate of coke or carbon formation. The invention described herein is a catalyst that addresses this requirement. Such a catalyst would reduce the frequency with which the catalyst needs to be regenerated. An additional advantage of the invention is that in a surprising and unexpected manner the catalyst has improved selectivity to light olefin production. Another advantage of the catalyst described herein is that the amount of coke produced is reduced when compared to using ZSM-5 and ZSM-35 catalysts alone under the same operating conditions.

SUMMARY OF THE INVENTION

In accordance with an aspect of the present invention, there is provided a composition comprising a mixture of two zeolite catalysts. Such a composition has previously unrecognized performance advantages over existing catalysts with respect to coke formation rate, selectivity towards ethylene and propylene production, and catalyst life.

In a non-limiting embodiment, one or more zeolites are combined to form a mixture that has improved capability of catalyzing the production of olefins from a feed comprising dimethyl ether, or methanol, and/or a methanol and dimethyl ether mixture.

In another non-limiting embodiment, one or more zeolites are combined to form a mixture that has improved capabilities of catalyzing the production of olefins from oxygenated hydrocarbons.

An object of the present invention is to provide a more robust catalyst composition having a reduced tendency to form coke when used for light olefin synthesis. The light olefins which may be synthesized include, but are not limited to, ethylene, propylene, and mixtures thereof.

A further object of the present invention is to use a mixture of light organic oxygenated compounds to synthesize light olefins.

Another object of the present invention is to provide a catalyst that has increased catalytic activity for producing light olefins from methanol.

Yet another object of the present invention is to provide a catalyst that comprises two or more zeolites that together have a synergic effect and reduce the rate of coke formation.

Another object of the present invention is to provide a catalyst that comprises two or more zeolites that together have a synergistic effect and reduce the rate of coke formation while producing predominantly more propylene than ethylene.

A further object of the present invention is to provide a catalyst that comprises two zeolites that together have a synergistic effect and reduce the rate of catalyst deactivation when used for converting methanol to olefins.

Another object of the present invention is to provide a catalyst that comprises two zeolites that together have a synergistic effect and reduce the rate of catalyst deactivation when used for converting methanol and dimethyl ether to olefins or light olefins.

Another object of the present invention is to provide a catalyst that comprises two or more zeolites that together produce olefins wherein the olefins are ethylene and propylene.

Another object of the invention is to provide a catalyst that comprises two or more zeolites that together have a synergistic effect on the conversion of dimethyl ether to olefins.

Another object of the invention is to provide a catalyst that comprises two or more zeolites that together have a synergistic effect on the conversion of dimethyl ether to olefins and increases the conversion to about 90%.

In a non-limiting embodiment, the catalyst comprises ZSM-5 and ZSM-35.

An object of the present invention is to produce a catalyst that retains catalytic activity for a longer period than a single zeolite, such as, for example, a longer period than ZSM-5 alone, and thus reduces the number of catalyst regenerations.

Another object of the present invention is to produce an extruded catalyst containing two zeolites that when combined have improved catalytic properties for the conversion of dimethyl ether to light olefins.

Another object of the present invention is to produce an extruded catalyst containing two zeolites that when combined have improved catalytic properties for the conversion of methanol and dimethyl ether to light olefins.

Another object of the present invention is to produce an extruded catalyst or a catalyst extrudate, containing two zeolites that when combined have improved catalytic properties for the conversion of methanol, water, and dimethyl ether to light olefins.

In a non-limiting embodiment, the composition further comprises a binder, and the zeolite catalysts are mixed with a binder to form an extruded catalyst or catalyst extrudate. In a non-limiting embodiment, the binder is selected from the group consisting of silicas, including colloidal silicas and amorphous silicas, clays, alumina, including amorphous alumina, and mixtures thereof.

Another object of the present invention is to provide a catalyst or catalyst extrudate with a high mesoporosity.

In another non-limiting embodiment of the invention, the extrusion process retains the high mesoporosity of the included zeolite structures.

In another non-limiting embodiment, the zeolite comprises a mixture of ZSM-5 and ZSM-35.

In another non-limiting embodiment, the zeolite comprises a mixture of MFI and ZSM-35 zeolite.

In a further non-limiting embodiment, the zeolite comprises a mixture of ZSM-5 and FER zeolite.

In yet another non-limiting embodiment, the zeolite comprises a mixture of MFI and FER zeolite.

In another non-limiting embodiment, the catalyst extrudate is formed using a binder.

In another non-limiting embodiment, the binder is amorphous silica.

In another non-limiting embodiment, extrudate is cross-linked using an ammonium nitrate salt.

In another non-limiting embodiment, the extruded catalyst is prepared from a silica solution.

In further non-limiting embodiment, the extruded catalyst is prepared from a silica sol with particle sizes of about 12 nm.

In another non-limiting embodiment, the binder is an inorganic binder of amorphous silica or amorphous alumina or a combination of both.

In a non-limiting embodiment, the binder is silica.

In a non-limiting embodiment, the binder is silica from colloidal silica.

In a non-limiting embodiment, the binder is amorphous silica.

In a non-limiting embodiment, the binder is clay.

In a non-limiting embodiment, the binder is amorphous alumina.

In another non-limiting embodiment, the binder is a mixture of one or more of silica, amorphous silica, clay, and amorphous alumina.

In another non-limiting embodiment, the binder is an inert binder or an inorganic binder which does not have catalytic activity.

In yet another non-limiting embodiment, the inert binder is an inorganic binder that includes one or more of alumina, silica, amorphous silica, amorphous alumina or a binder derived from colloidal silica.

In a non-limiting embodiment, the binder imparts additional catalytic activity to the catalyst mixture.

Another object of the present invention is to provide a process to produce an extruded catalyst containing at least two zeolites that when combined have improved catalytic properties for the conversion of dimethyl ether and water into light olefins.

Another object of the present invention is to provide a catalyst that has improved selectivity towards the formation of ethylene.

Another object of the present invention is to provide a catalyst that has improved selectivity towards the formation of propylene.

Another object of the present invention is to provide a catalyst that has improved selectivity towards the formation of ethylene and propylene.

Yet another object of the present invention is to produce a catalyst for producing light olefins from dimethyl ether.

A further object of the present invention is to produce a catalyst for producing light olefins from a mixture of dimethyl ether and water.

Another object of the present invention is to produce a catalyst for producing light olefins from a reaction mixture of dimethyl ether, water, and methanol.

Another object of the present invention is to provide a method for producing a catalyst that has a reduced tendency to deactivate during the synthesis of light olefins from dimethyl ether, water, and methanol.

Yet another object of the present invention is to provide a method for producing a catalyst that has a reduced tendency to deactivate as a result of coke formation during the synthesis of light olefins from dimethyl ether, water, and methanol.

Another object of the present invention is to provide a method for producing a catalyst that has improved performance and reduced tendency to deactivate as a result of coke formation and an increased resistance to coke formation during the synthesis of light olefins from dimethyl ether, water, and methanol.

Another object of the present invention is to provide a method for using the catalyst for the conversion of dimethyl ether into light olefins.

Another object of the present invention is to provide a catalyst that has an increased resistance to deactivation.

Another object of the present invention is to provide a catalyst composition that comprises a mixture of ZSM-5 and ZSM-35 zeolites.

Another object of the present invention is to provide a catalyst composition that comprises a mixture of ZSM-5 and ZSM-35 zeolite formed into an extrusion.

Yet another object of the present invention is to provide a process for manufacturing the extruded catalyst.

Another object of the present invention is to provide a catalyst mixture that reduces the amount of coke formation from about 23 to about 46% the amount of coke produced if ZSM-5 were used alone and under similar operating conditions.

Another object of the present invention is to provide a more robust catalyst that is resistant to coke formation, for light olefin synthesis from a mixture of dimethyl ether, water, and methanol.

In a non-limiting embodiment, the catalyst used for light olefin synthesis from methanol, dimethyl ether and water comprises ZSM-5 and ZSM-35 zeolites, and a binder.

In another non-limiting embodiment, the catalyst used for light olefin synthesis from methanol, dimethyl ether, and water comprises ZSM-5 and ZSM-35 zeolites, and an inert binder.

In a non-limiting embodiment, light olefin(s) is (are) synthesized from a mixture of methanol, dimethyl ether, and water is the presence of a catalyst that comprises ZSM-5 and ZSM-35 zeolites and a binder.

In another non-limiting embodiment, light olefin(s) is (are) synthesized from a mixture of methanol, dimethyl ether, and water is the presence of a catalyst that comprises of ZSM-5 and ZSM-35 zeolites and an inert binder.

In a non-limiting embodiment, ZSM-5 zeolite is present in an amount of from about 10 wt. % to about 95 wt. % of the total amount of zeolite in the composition.

In a non-limiting embodiment, ZSM-5 is present in an amount of from about 10 wt. % to about 90 wt % of the total amount of zeolite in the composition.

In another non-limiting embodiment, ZSM-5 is present in an amount of from about 40 wt. % to about 90 wt. % of the total amount of zeolite in the composition, in a further non-limiting embodiment, ZSM-5 is present in an amount of from about 55 wt. % to about 85 wt. % of the total amount of zeolite in the composition.

In a non-limiting embodiment, ZSM-35 is present in an amount of from about 5 wt. % to about 90 wt. % of the total amount of zeolite in the composition.

In another non-limiting embodiment, ZSM-35 is present in an amount of from about 10 wt. % to about 90 wt. % of the total amount of zeolite in said composition.

In another non-limiting embodiment, ZSM-35 is present in an amount of from about 10 wt. % to about 60 wt. % of the total amount of zeolite in the composition.

In yet another non-limiting embodiment, ZSM-35 is present in an amount of from about 15 wt % to about 45 wt. % of the total amount of zeolite in the composition.

In a non-limiting embodiment, the catalyst used in the synthesis of light olefins includes ZSM-5 dispersed in a binder.

In a non-limiting embodiment, the catalyst used in the synthesis of light olefins includes at least ZSM-35 dispersed in a binder.

In another non-limiting embodiment, the catalyst used in the synthesis of light olefins includes at least ZSM-5 and ZSM-35 dispersed in a binder.

In a non-limiting embodiment, the catalyst comprises a mixture of extruded ZSM-5 and ZSM-35 having a high mesoporosity. The catalyst mixture provides a reduction in the amount of carbon formation by about 23 to 46% compared to ZSM-5 based zeolite alone. The catalyst also reduces the rate of coke formation by 23 to 46% in comparison to ZSM-5.

In a non-limiting embodiment of the invention the molar percent of ethylene product to the total amount of ethylene and propylene produced is about 23% while conversely the molar percent of propylene to the total amount of ethylene and propylene produced is about 77%.

In a non-limiting embodiment, one or more of the dimethyl ether and methanol used for the synthesis of olefins are obtained from renewable or sustainable sources.

In a non-limiting embodiment, renewable sources of syngas for producing the methanol or dimethyl ether include agricultural crop residues and waste, urban municipal waste, industrial organic residues, and construction and demolition waste.

In a non-limiting embodiment, renewable sources of syngas which may be used to produce the methanol or dimethyl ether can be biomass, municipal waste, construction wastes, forest waste residues, or any other sustainable source of carbon containing material.

In a non-limiting embodiment, oxygenated hydrocarbons comprise the feed to the reactor.

The oxygenated hydrocarbons include methanol and dimethyl ether.

In a non-limiting embodiment, the ZSM-5 zeolite is dispersed in a binder having a mesoporous volume of at least 0.07 cm$^3$/g-zeolite and may be greater than 0.10 cm$^3$/g-zeolite.

In a non-limiting embodiment, the ZSM-35 zeolite is dispersed in a binder having a mesoporous volume of at least 0.03 cm$^3$/g-zeolite and may be greater than 0.10 cm$^3$/g-zeolite.

In a non-limiting embodiment, is a mixture of ZSM-5 and ZSM-35 is dispersed in a binder and has a mesoporous volume of at least 0.03 cm$^3$/g-zeolite and may be greater than 0.10 cm$^3$/g-zeolite.

In a non-limiting embodiment, a mixture of ZSM-5 and ZSM-35 is dispersed in a binder to give an average pore diameter between 9.1 and 9.3 nm.

In a non-limiting embodiment, a mixture of ZSM-5 and ZSM-35 is dispersed in a binder and has a specific surface area between about 324 to 410 m$^2$/g catalyst.

In a non-limiting embodiment, the mixed zeolite catalyst, which may be in extruded form, is subjected to a cross-linking process by contacting the catalyst with ammonium nitrate, and then the catalyst is calcined.

DETAILED DESCRIPTION OF THE INVENTION

The following terms are defined below:

DME—Dimethyl ether.

IMPCA—International Methanol Producers and Consumers Association.

FER—a group of zeolite materials comprising forms of ZSM-35 zeolite.

Mordenite Framework Inverted, or MFI—a group of zeolite materials comprising forms of ZSM-5 zeolite.

WHSV—Weight Hourly Space Velocity as the weight of feed per hour per unit weight of catalyst loaded in the reactor.

medium pore size zeolites—a group of zeolites classified on the size of the pore structure, which includes ZSM-5 and ZSM-35.

Renewable material used for producing methanol and dimethyl ether is gasified by any known means such as the methods and processes described in U.S. Pat. Nos. 8,137,655 and 8,192,647. Synthesis gas produced in the gasification process is used for the methanol synthesis. The production of methanol from syngas is carried out at a temperature in the range of about 200 to 300° C. and a pressure range of about 20 to 100 bar over a catalyst including mixed oxides of copper, zinc and chromium, and copper zinc aluminum oxide catalyst as described in U.S. Pat. No. 3,326,956.

Catalysts used for methanol synthesis are available commercially with details of manufacture given in U.S. Pat. No. 3,840,478 wherein the manufacture of copper oxide-zinc oxide and chromium oxide catalysts for methanol synthesis are described.

The synthesis gas used for manufacturing the methanol can also be obtained from any other known method for producing syngas, such as' steam, partial oxidation, or autothermal reforming of hydrocarbons or other carbon sources including natural gas.

Reactant dimethyl ether, (DME), is produced by dehydrating methanol over commercially available acid catalyst. It is not necessary for the methanol used for dimethyl ether synthesis to be pure. Methanol with a purity of 99.85% as defined by the IMPCA reference specification for methanol, can be used or a less pure methanol such as 70-80% w/w of methanol with a 20-30% w/w water content can be used as the methanol source for the dehydration reaction.

Synthesis gas produced from renewable materials through gasification technology, can be used to synthesize dimethyl ether directly. This process is referred to as the "one step dimethyl ether production process". Methods for direct synthesis of dimethyl ether from synthesis gas are described in EP2028173 and US2015/0018582.

EP2028173 describes a catalytic process for the conversion of syngas consisting of carbon monoxide, carbon dioxide and hydrogen to dimethyl ether in a catalytic process comprising contacting a stream of synthesis gas comprising carbon dioxide in a first dimethyl ether synthesis step with one or more catalysts active in the formation of methanol and the dehydration of methanol to dimethyl ether to produce a product comprising dimethyl ether, methanol, carbon dioxide and unconverted synthesis gas, and washing the product mixture comprising carbon dioxide and unconverted synthesis gas in a scrubbing zone with a liquid solvent.

The solid catalyst extrudate is used for the production of a product comprising light olefins from a feed mixture that contains one or more of methanol and dimethyl ether and optionally water at reaction conditions that produce light olefins. The solid catalyst extruded form comprises a mixture of two different zeolites and an inert binder such that the combination of zeolites results in an improved and positive synergistic effect on catalytic performance and a reduced rate of coke formation that otherwise would not be realized if the individual zeolite simply were mixed or layered in a reactor and not in intimate contact within a single catalyst form and bound by a porous inert binder.

In a non-limiting aspect of this invention, light olefins are synthesized from a mixture of dimethyl ether, water, and methanol. The reaction is carried out at a temperature of from about 200 to 500° C. and at atmospheric or higher pressures.

The reaction is carried out in a reactor that is a catalytic fixed bed, a fluidized bed, a tubular reactor, or other type of reactor into which the catalyst can be placed.

In a non-limiting embodiment, the catalyst used for the synthesis of light olefins from dimethyl ether and methanol and water mixture, comprises ZSM-5 and ZSM-35 and a binder.

In a non-limiting embodiment, the catalyst used for the synthesis of light olefins is in an extruded form.

A another non-limiting embodiment, is that the catalyst used for the synthesis of light olefins is pelletized.

In yet another non-limiting embodiment, the extruded catalyst herein described that is used for the synthesis of light olefins is in the form of small solid cylinders or spheres.

In another non-limiting embodiment, one form of the ZSM-5 zeolite dispersed in the binder for light olefins synthesis is an MFI type zeolite as described in the "Atlas of Zeolite Framework types", D H Olson, Ch. Baerlocher et al., 6th edition, 2007, wherein such atlas states that ZSM-5 zeolites are tridimensional zeolites with pore aperture dimensions of 5.1×5.7 Å and 5.3×5.6 Å.

In another non-limiting embodiment, one form of the ZSM-35 zeolite dispersed in the binder has specific properties and characteristics for olefin synthesis, and is an MFI type zeolite described in the "Atlas of Zeolite Framework types", DH Olson, Ch. Baerlocher et al., 6th edition, 2007. ZSM-35 is a tridimensional zeolite with pore aperture dimension of 5.5×4.3 Å and 4.8×3.4 Å.

Both ZSM-5 and ZSM-35 are in a class of zeolites that is referred to as medium pore size zeolites.

The zeolite powder materials are mixed in suitable proportions as herein described and mixed with a binder. The resulting mixture is then formed into an extrudate which is then shaped before being dried and calcined to give the calcined catalyst. The calcined catalyst is then cross linked by adding ammonium nitrate, drying and then calcined a second time. The resulting extruded form is the cross-linked catalyst and also is the activated catalyst. The ammonium nitrate and calcination steps activate the catalyst.

Mixing the zeolites in this way and forming them into a single catalyst extrudate results in a hybrid catalyst which also can be referred to as a hybrid zeolite catalyst.

The hybrid catalyst is produced, in a non-limiting embodiment, by mixing powder forms of the zeolites as herein described, followed by dispersing the mixture of zeolite powders in water and then adding colloidal silica to form a first dispersion, and adding hydroxyethylcellulose to the mixture to form a first plastic paste. The paste then is passed through an extrusion die and cut to give uniformly sized cylindrical catalyst forms. The cylindrical catalyst forms are allowed to dry at room temperature before being calcined in an oven to about 550° C. to provide a calcined catalyst.

The calcined catalyst is used in a reactor for the conversion of dimethyl ether to olefins as described herein.

The catalyst produced in this manner was found to have improved performance with respect to carbon formation. The catalyst showed an improved capacity for reduced coke formation with one combination of ZSM-5 and ZSM-35 presenting surprising results that would not have been expected.

In a non-limiting embodiment of the invention, the performance of the catalyst and its selectivity towards producing olefins was measured in a fixed catalytic bed. Oxygenated hydrocarbons such as methanol and dimethyl ether were used in the experiments for testing the catalysts. Methanol, dimethyl ether and water were mixed in a fixed-bed reactor at temperatures from about 400 to about 515° C. with Weight Hourly Space Velocities in the range of from about 15 to about $50h^{-1}$. The catalyst was found to have exhibited high conversion and selectivity toward light olefins while demonstrating a reduced susceptibility to the loss of activity because of coke and carbon formation.

In a non-limiting embodiment, the water content in the feed to the reactor is from about 25 wt. % to about 60 wt. %.

In another non-limiting embodiment, the water content in the feed to the reactor is from about 30 wt. % to about 40 wt. %.

In a further non-limiting embodiment, the temperature of the reaction in the reactor is from about 250° C. to about 500° C.

In another non-limiting embodiment, the temperature of the reaction in the reactor is from about 400° C. to about 500° C.

In a non-limiting embodiment, the gas hourly space velocity is from about 15 to about 50 $h^{-1}$.

EXAMPLES

Embodiments of the present invention are further illustrated by the non-limiting examples which follow. It is to be understood, however, that the scope of the present invention is not intended to be limited thereby.

Example 1

Two commercial zeolites, NH$_4$ ZSM-5 and NH$_4$ FER, were supplied by Zeolyst International in powder form. These were used to manufacture a number of extruded catalysts with varying loadings of zeolite.

The hybrid catalyst extrusions used for testing and demonstrating the performance of the catalyst were prepared as described below.

An aliquot of each catalyst was weighed in an appropriate proportion so as to give the desired weight ratio for each zeolite in the final extrusion.

The NH$_4$ ZSM-5 and NH$_4$ FER zeolites powder aliquots then were mixed together for 10 minutes.

A colloidal silica (W.R. Grace, Ludox™ HS-40) solution then was added to the zeolite mixture with agitation and the resulting solution was mixed for a further 10 minutes. The colloidal silica was used as a binder for the zeolites and adds strength to the resulting extrudate.

Sufficient colloidal silica was added to the mixture so that the dry form of the extrudate would contain 75% (w/w) zeolite and 25% (w/w) silica on a dry basis. For example when using a colloidal silica solution supplied as a 40% weight solution of silica, 100 g of colloidal silica solution is added to every 120 g of dry zeolite mixture to give a suspension of zeolite and colloidal silica.

An about 8.5% (w/w) solution hydroxyethylcellulose solution was prepared by dissolving the polymer in deionized water with mixing for 10 minutes or until the solid had dissolved.

The hydroxyethylcellulose adds a degree of plasticity to the unformed extrudate of the catalyst mixture. An optimal liquid/solid relationship of 0.6 was used and found to be effective.

98 g of the hydroxyethylcellulose solution then was mixed with the zeolite-colloidal silica mixture and mixing continued for at least 20 minutes after which time it gave a smooth paste blend.

The hydroxyethylcellulose is added as a temporary binder to bind the solid particles of the dispersion and form a paste with plastic properties that allow the paste to be formed and extruded into a stable shape.

The smooth paste blend then was passed through an extrusion die to give cylindrical sticks with a diameter of about 3 to 4 mm and lengths of about 10 to 30 cm. The extruded forms then were cut into about 3 to 5 mm long pellets that were then allowed to dry at room temperature for 24 h.

The dried catalyst pellets then were placed in a calcination oven at room temperature. The calcination process heated the oven from room temperature up to about 550° C. with a heating ramp of 2° C./minute. The catalyst then was left to stand in the oven at 550° C. for 3 hours or more. After this time the calcined catalyst was allowed to cool slowly with the oven to give the calcined extrudate.

After cooling, a nitrate impregnation and crosslinking process was used to activate the catalyst. The calcined extrudate so produced was mixed with a 2M aqueous ammonium nitrate (NH$_4$NO$_3$) solution. The solution was maintained at 55° C. with 100 ml of nitrate solution added per 10 g of calcined extrudate used. The resulting nitrate impregnated calcined extrudate solid material was then left to dry in air for 4 h.

The resulting nitrate impregnated dry calcined extrudate was then calcined a second time using a similar process to the first. The dry nitrated impregnated calcined extrudate was placed in an oven at room temperature and heated to a temperature of 550° C. at a rate of 2° C./minute and then allowed to soak at 550° C. for 3 hours. The extrudates were allowed to cool with the oven and then placed in a desiccator.

This catalyst preparation process herein described produced an activated solid, compression resistant catalyst that could be used directly in a reactor.

The resulting solid calcined catalyst particles were removed from the oven and allowed to cool in a desiccator in a nitrogen purged atmosphere. The catalyst particles were uniform in shape and size with sufficient strength to resist compression.

The calcined cross-linked catalyst form was then allowed to cool slowly with the oven, before being removed and stored in a desiccator until used Table 1 shows the composition and combinations of each component and zeolite in the catalyst particles manufactured using this process. Table 2 shows the sample identifiers and composition of each of the catalyst prepared and the amount of each zeolite used for each on a dry basis of calcined catalyst.

TABLE 1

Extrusion sample preparation - material compositions before drying.

| Material | Weight g |
|---|---|
| Total Zeolite | 187.5 |
| 40% Colloidal silica (Ludox-HS40) | 156.25 |
| Hydroxyethylcellulose | 12.75 |
| Water | 43.5 |

TABLE 2

Mixed Zeolite Catalyst Sample Composition - excluding Binder.

| Catalyst Name | Weight Percentage Zeolite % | | Weight Zeolite g | |
|---|---|---|---|---|
| | FER | ZSM-5 | FER | ZSM-5 |
| 100-H-ZSM-5 | 0 | 100 | 0 | 187.5 |
| Hybrid I | 10 | 90 | 18.75 | 168.75 |
| Hybrid II | 20 | 80 | 37.5 | 150 |
| Hybrid III | 40 | 60 | 75 | 112.5 |
| Hybrid IV | 60 | 40 | 112.5 | 75 |
| 100-H-FER | 100 | 0 | 187.5 | 0 |

Example 2

The catalysts produced in Example 1 were analyzed using a number of techniques to quantify the structure, surface area, and pore sizes within the catalyst. This was done to confirm that the pore structure had not changed significantly during the preparation of the mixed catalyst extrudate.

Table 3 shows the results obtained in these measurements and a number of conclusions and observations can be drawn from these data. The percentage crystallinity between the pure catalyst and the extruded form of the pure catalyst appears to change in line with the ratio of binding material and zeolite loading. The binding material, present as silica, would be expected to be present as an amorphous material after classification.

TABLE 3

Catalyst Properties and Characterization Results.

| | Weigh % Zeolite | | % | N$_2$ Adsorption (cm$^3$/g zeolite) | | BET Surface Area | PORE SIZE |
|---|---|---|---|---|---|---|---|
| | FER | ZSM-5 | Crystallinity | V$_{micro}$ | V$_{meso}$ | m$^2$/g | (nm) |
| H-ZSM5 (P) | — | 10 | 100 | 0.12 | 0.06 | 409.84 | 5.5 |
| H-ZSM5 (E) | — | 10 | 75 | 0.13 | 0.14 | 329.48 | 9.2 |
| H-FER (P) | 10 | — | 100 | 0.12 | 0.02 | 361.8 | 9.2 |
| H-FER (E) | 10 | — | 75 | 0.13 | 0.13 | 324.33 | 9.2 |
| Hybrid I (E) | 1 | 9 | | 0.13 | 0.13 | 324.57 | 9.24 |
| Hybrid II (E) | 2 | 8 | | 0.13 | 0.14 | 329.5 | 9.22 |
| Hybrid III (E) | 4 | 6 | | 0.13 | 0.14 | 332 | 9.27 |
| Hybrid IV (E) | 6 | 4 | | 0.13 | 0.14 | 329.5 | 9.23 |

E: Extruded,
P: Powder

It is surprising to note that after mixing and calcination, the catalysts all have a pore size that is about 9.2 nm. This remains the case when 90% of the catalyst is made up of ZSM-5, which has an average pore size of 5.5 nm before being incorporated in the catalyst extrudate.

The catalyst produced using the method of Example 1 with the compositions given in Table 4 each were tested in a reactor with various feed mixtures containing dimethyl ether, water, and methanol. The methanol and dimethyl ether to olefin reaction conditions at which each catalyst was tested are given in Table 5. The methanol, water, and dimethyl ether feed composition was kept constant in these reactions while the reactions were done at atmospheric pressure.

TABLE 4

Mixed Zeolite Catalyst Sample Composition with binder.

| Catalyst | Weight Percentage % | | | Weight of component g | | |
|---|---|---|---|---|---|---|
| Name | FER | ZSM-5 | Silica | FER | ZSM-5 | Silica |
| 100-H-ZSM-5 | 0 | 75 | 25 | 0 | 187.5 | 62.5 |
| Hybrid I | 7.5 | 67.5 | 25 | 18.75 | 168.75 | 62.5 |
| Hybrid II | 15 | 60 | 25 | 37.5 | 150 | 62.5 |
| Hybrid III | 30 | 45 | 25 | 75 | 112.5 | 62.5 |
| Hybrid IV | 45 | 30 | 25 | 112.5 | 75 | 62.5 |
| 100-H-FER | 75 | 0 | 25 | 187.5 | 0 | 62.5 |

TABLE 5

Methanol to olefin reaction operating conditions.

| | | Feed composition (wt. %) | | |
|---|---|---|---|---|
| Temperature (° C.) | WHSV (h$^{-1}$) | MeOH | DME | Water |
| 400 | 15 | 5 | 60 | 35 |

All reactions were done at atmospheric pressure.

The results for each case were tabulated in Table 6. The sample containing 20% HFER and 80% HZSM shows a capability that is surprising and unexpected relative to the other catalyst compositions. This formulation of catalyst demonstrates ability for increased dimethyl ether conversion, with up to about 90.2% conversion which is a significant improvement compared to the other catalyst mixtures and the catalysts containing only a single zeolite. This performance was surprising and would not and could not have been predicted from the data obtained for the other mixtures. It is clear the having both zeolites present at this ratio has a significant and measurable synergic effect on catalyst performance.

TABLE 6

Product distribution by molar percentage after 350 minutes reaction time on hybrid catalyst mixtures of H-ZSM-5 (HZSM) and H-ZSM-35 (HFER).

| | HZSM (280) Mol % | HFER (20) Mol % | 10 HFER-90 HZSM Mol % | 20 HFER-80 HZSM Mol % | 40 HFER-60 HZSM Mol % | 60 HFER-40 HZSM Mol % |
|---|---|---|---|---|---|---|
| C$_1$-C$_4$ | 0.0 | 0.0 | 0.0 | 0.0 | 0.0 | 0.0 |
| C$_2$= | 13.04 | 92.98 | 30.17 | 16.24 | 32.49 | 23.48 |
| C$_3$= | 56.61 | 2.05 | 40.60 | 53.29 | 30.69 | 38.85 |
| C$_4$= | 6.75 | 0.66 | 4.29 | 6.98 | 6.24 | 9.06 |
| C$_5^+$= | 3.63 | 1.26 | 4.33 | 5.06 | 5.96 | 6.52 |
| Paraffin's (C$_5^+$) | 14.34 | 1.63 | 14.56 | 13.24 | 17.30 | 14.93 |
| Naphtha's (C$_5^+$) | 1.50 | 0.40 | 1.04 | 1.63 | 1.43 | 2.07 |
| Aromatics | 4.13 | 1.01 | 5.00 | 3.56 | 5.89 | 5.09 |
| Conversion DME after 5 hours | 82.6 | 34.6 | 70.7 | 90.2 | 71.1 | 87.3 |
| Coke (wt. %) | 1.48 | 5.7 | 1.49 | 1.14 | 0.8 | 1.25 |

It also is seen that the 20% HFER-80% HZSM catalyst mixture also produces a product mixture that contains about 53.3% propylene, which is significantly more than any of the other mixtures. The single zeolite version of the catalyst is the only catalyst that produces more than 53.3% propylene. The 20% HFER-80% HZSM catalyst mixture also produced less aromatic compounds in the product mixture while also not producing the lowest carbon formation rate of the catalyst tested. This mixture did have a slower rate of carbon formation than either of the catalysts produced using only one zeolite. The carbon produced after 5 hours of operation was about 1.14 wt. % on the catalyst.

Example 3

The catalysts were tested in a fixed bed stainless steel reactor (2.03 cm i.d, length=100 cm). The catalyst samples were conditioned in situ by heating them to 515° C. at a rate of 5° C./minute under nitrogen with a flow of 200 actual milliliters minute measured at laboratory conditions. The catalysts then were kept at to 515° C. for 5 h or more.

The catalyst temperature then was set to the required experiment temperature, Table 5, and allowed to equilibrate. All the catalyst formulations were exposed to a given feed composition for a continuous 5 hour periods. Liquid methanol and water was mixed with a metered amount of dimethyl ether. The resulting mixture was then fed into the top of the reactor and passed down through the catalyst bed before leaving the reactor.

The hot vapor reaction product vapor mixture leaving the reactor then was cooled to 30° C. before liquid and vapor fractions were separated into a vapor stream and a liquid stream. Analysis of these streams showed that the liquid stream was a mixture of water, and organic compounds while the vapor stream was a mixture of non-condensable hydrocarbon vapors.

All process runs resulted in 100% conversion of the feed methanol and up to about 90.2% conversion of dimethyl ether, with conversion being calculated as the ratio of {the number of moles of feed component less the number of feed component in the reaction product} to the number of feed component in the feed.

The conversion of dimethyl ether was between 34.6 and 90.2 wt. %. Hybrid catalyst containing 80 wt. % ZSM and 20 wt. % FER resulted in a dimethyl ether conversion of about 90.2 wt. %. A hybrid catalyst consisting of 40 wt % ZSM and 60 wt. % FER that gave a dimethyl ether conversion of about 87.3 wt. %.

The preceding example(s) can be repeated with similar success by substituting the various components and configurations for each zeolite as described herein.

Although the invention has been described in detail with particular reference to a number of embodiments, embodiments can be derived at that give the same or similar results. Upon studying this application it will be possible that those skilled in the art will realize other equivalent variations and/or modifications. It is intended that the claims contained in any patent issued on this application cover all such equivalents. The entire disclosures of all references, applications, patents, and publications cited above are hereby incorporated herein by reference to the same extent as if each patent, patent application, and reference were incorporated individually by reference.

It is to be understood, however, that the scope of the present invention is not to be limited to the specific embodiments described above. The invention may be practiced other than as particularly described, and still be within the scope of the accompanying claims.

What is claimed is:

1. A method of producing at least one olefin from dimethyl ether, comprising:
reacting a feed comprising dimethyl ether under catalytic conversion conditions in the presence of a composition comprising at least one catalyst particle, wherein each of said at least one catalyst particle(s) contains a ZSM-5 zeolite, a ZSM-35 zeolite, and a binder, to produce a product comprising at least one olefin.

2. The method of claim 1 wherein said feed further comprises methanol.

3. The method of claim 2 wherein said feed further comprises water.

4. The method of claim 1 wherein said at least one olefin is ethylene.

5. The method of claim 1 wherein said at least one olefin is propylene.

6. The method of claim 1 wherein said at least one olefin comprises ethylene and propylene.

7. The method of claim 1 wherein said ZSM-5 zeolite is present in an amount of from about 10 wt. % to about 95 wt. % of the total amount of zeolite in said composition.

8. The method of claim 7 wherein said ZSM-5 zeolite is present in an amount of from about 10 wt. % to about 90 wt. % of the total amount of zeolite in said composition.

9. The method of claim 8 wherein said ZSM-5 zeolite is present in an amount of from about 40 wt % to about 90 wt. % of the total amount of zeolite in said composition.

10. The method of claim 9 wherein said ZSM-5 zeolite is present in an amount of from about 55 wt. % to about 85 wt. % of the total amount of zeolite in said composition.

11. The method of claim 1 wherein said ZSM-35 zeolite is present in an amount of from about 5 wt. % to about 90 wt. % of the total amount of zeolite in said composition.

12. The method of claim 11 wherein said ZSM-35 zeolite is present in an amount of from about 10 wt. % to about 90 wt. % of the total amount of zeolite in said composition.

13. The method of claim 12 wherein said ZSM-35 zeolite is present in an amount of from about 10 wt. % to about 60 wt. % of the total amount of zeolite in said composition.

14. The method of claim 13 wherein said ZSM-35 zeolite is present in an amount of from about 15 wt. % to about 45 wt. % of the total amount of zeolite in said composition.

15. The method of claim 1 wherein said binder is selected from the group consisting of silicas, clays, aluminas, and mixtures thereof.

16. The method of claim 15 wherein said binder is a silica.

17. The method of claim 16 wherein said silica is derived from colloidal silica.

18. The method of claim 16 wherein said silica is an amorphous silica.

19. The method of claim 15 wherein said binder is a clay.

20. The method of claim 15 wherein said binder is an alumina.

21. The method of claim 20 wherein said alumina is an amorphous alumina.

* * * * *